US00PP33681P2

(12) United States Plant Patent
Hanes

(10) Patent No.: US PP33,681 P2
(45) Date of Patent: Nov. 23, 2021

(54) ***PELARGONIUM* PLANT NAMED 'PEQZ0092'**

(50) Latin Name: *Pelargonium interspecific*
Varietal Denomination: PEQZ0092

(71) Applicant: SYNGENTA CROP PROTECTION AG, Basel (CH)

(72) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/078,943

(22) Filed: Oct. 23, 2020

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0092' particularly distinguished by the scarlet orange colored inflorescences held above the green foliage that has a darker green zone. 'PEQZ0092' is very heat and drought tolerant with continuous color through the most extreme summer heat, and exceptional edema tolerance on a well-branched plant habit.

1 Drawing Sheet

Latin name of the genus and species of the plant claimed: *Pelargonium interspecific.*

Varietal denomination: 'PEQZ0092'.

BACKGROUND OF THE NEW PLANT

The present invention comprises a new *Pelargonium*, botanically known as *Pelargonium interspecific*, and hereinafter referred to by the variety name 'PEQZ0092'.

'PEQZ0092' is a product of a planned breeding program. The new cultivar 'PEQZ0092' has scarlet orange colored inflorescences held above the green foliage that has a darker green zone, very heat and drought tolerant with continuous color through the most extreme summer heat, and exceptional edema tolerance on a well-branched plant habit.

'PEQZ0092' originates from a hybridization in a controlled breeding program made in September 2012 in a greenhouse in Gilroy, Calif. The female parent was an unpatented, proprietary plant of *P. interspecific* parentage, identified as '11491-1V' with lighter green leaves, with apple blossom semi-double florets and a more compact plant habit when compared to 'PEQZ0092'.

The male parent of 'PEQZ0092' was an unpatented, proprietary plant of *P. interspecific* parentage, identified as '11471-4V' with darker leaves and scarlet colored florets when compared to 'PEQZ0092'. The resultant seed was sown in July 2014.

'PEQZ0092' was selected as one flowering plant within the progeny of the stated cross in October 2014 in a greenhouse in Gilroy, Calif.

The first act of asexual reproduction of 'PEQZ0092' was accomplished when vegetative stem cuttings were propagated from the initial selection in the November 2014 in a greenhouse in Gilroy, Calif.

BRIEF SUMMARY OF INVENTION

Horticultural examination of plants grown from cuttings of the plant initiated in January 2015 in Gilroy, Calif., and continuing thereafter, has demonstrated that the combination of characteristics as herein disclosed for 'PEQZ0092' are firmly fixed and are retained through successive generations of asexual reproduction.

'PEQZ0092' has not been observed under all possible environmental conditions. The phenotype may vary significantly with variations in environment such as temperature, light intensity, and day length.

A Plant Breeder's Right for this cultivar has not yet been applied for. 'PEQZ0092' has not been made publicly available prior to the effective filing date of this application, notwithstanding any disclosure that may have been made less than one year prior to the effective filing date of this application by the inventor or another who obtained 'PEQZ0092' directly from the inventor.

The following traits have been repeatedly observed and are determined to be the basic characteristics of the new variety. The combination of the characteristics described herein distinguishes this *Pelargonium* as a new and distinct variety.

BRIEF DESCRIPTION OF THE PHOTOGRAPHS

The accompanying photographic drawings show typical flower and foliage characteristics of 'PEQZ0092' with colors being as true as possible with an illustration of this type.

Figure 1:
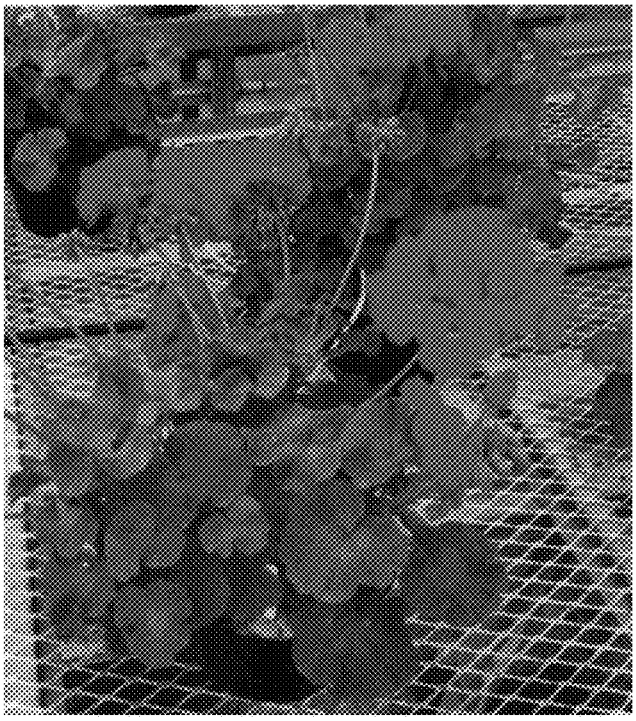
Figure 2:
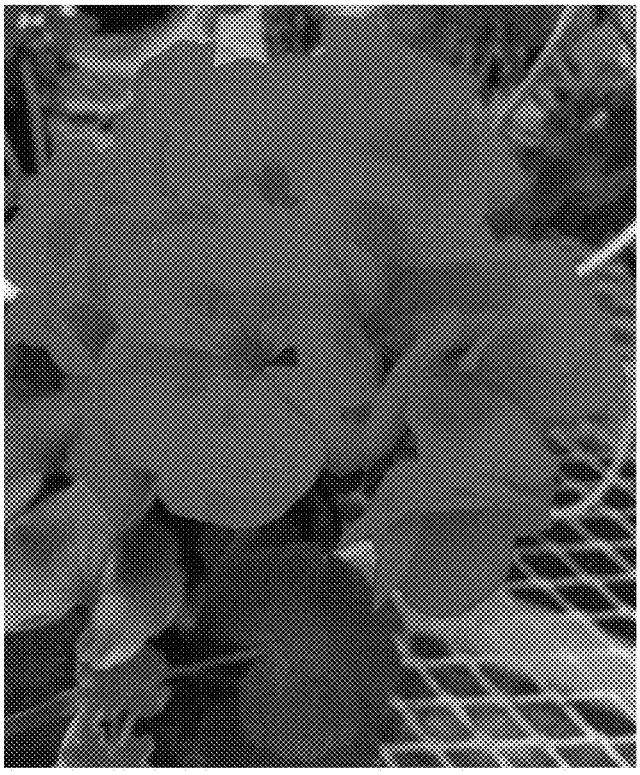

The photographic drawings show in FIG. 1, 3 flowering plants of the new variety and in FIG. 2, a close-up of an inflorescence. The plants were 28 weeks old.

DETAILED BOTANICAL DESCRIPTION

The plant descriptions and measurements were taken in Gilroy, Calif. in late September 2020 under natural light These plants were approximately 25 weeks old and were grown in a 1 gallon pots, in a greenhouse setting. The plants shown in the photographs were taken in October 2020.

Color references are made to The Royal Horticultural Society Colour Chart (R.H.S.) 2001.

TABLE 1

DIFFERENCES BETWEEN THE NEW VARIETY 'PEQZ0092' AND A MOST SIMILAR VARIETY

| | 'PEQZ0092' | 'PEQZ0049' (U.S. Plant Pat. No. 32,367) |
|---|---|---|
| Floret size: | Large | Large |
| Floret petal color: | Orange scarlet with spot | Coral with spot |
| Leaves: | Darker green with a green zone | Lighter green without zonation |
| Peduncle length: | Long | Shorter |

Plant:

*Form, growth and habit.*—Upright, outwardly spreading, heat and drought tolerant with continuous color through the most extreme summer heat, edema tolerance.

*Plant height.*—13-18 cm.

*Plant height (inflorescence included).*—25-30 cm.

*Plant width.*—27-32 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B.

Foliage:

*Immature leaf, color upper surface.*—RHS 137A with a disc of RHS 137B at the base of the leaf.

*Immature leaf, lower surface.*—RHS 137C.

*Mature leaf, color upper surface.*—RHS 137A.

*Mature leaf, color lower surface.*—RHS 137C.

*Length.*—5.9-6.2 cm.

*Width.*—8.5-9.0 cm.

*Shape.*—Cordate.

*Base shape.*—Cordate.

*Apex shape.*—Acute.

*Margin.*—Slightly dentate.

*Texture upper side.*—Smooth.

*Texture lower side.*—Smooth.

*Leaf zonation color.*—Darker green zone (RHS 137B) but not pigmented with anthocyanins.

*Conspicuousness of the zone of the leaf blade.*—Medium.

*Color of veins, upper surface.*—RHS 137C becoming indistinct.

*Color of veins, lower surface.*—RHS 137C becoming indistinct.

*Pattern of veining.*—Palmate.

*Petiole color.*—RHS 137C.

*Petiole length.*—5-6 cm.

*Diameter of petiole.*—0.25 cm.

*Texture.*—Smooth.

Stem:

*Quantity of branches.*—6-8.

*Color of stem.*—Between RHS 144A and RHS 144B.

*Length of stem.*—8-12 cm.

*Diameter.*—1.0 cm.

*Length of internodes.*—1.5 cm.

*Texture.*—Sparsely hirsute, pilose, glandular hairs.

Peduncle:

*Color of peduncle.*—RHS 137C.

*Length of peduncle.*—18-21 cm.

*Peduncle diameter.*—0.5 cm.

*Texture.*—Hirsute, glandular hairs.

Pedicel:

*Color of pedicel.*—Upper two thirds RHS 178B and bottom third RHS 145A.

*Length of pedicel.*—3.5 cm.

*Diameter of pedicel.*—0.2 cm.

*Texture.*—Sparsely pilose, glandular hairs.

Bud (just before opening):

*Color.*—Closest to RHS 34A.

*Length.*—2.0 cm.

*Width.*—0.9 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—12, with 15 immature umbels in various stages.

*Width of the inflorescence.*—5.8 cm.

*Fragrance.*—None.

*Umbel diameter.*—12-14.0 cm.

*Umbel depth.*—6.5-7.5 cm.

Corolla:

*Form.*—Semi-double.

*Number of petals.*—6-9.

*Diameter of flower.*—5.8 cm.

*Depth of flower.*—1.5 cm.

*Color upper petals, upper surface.*—RHS N30A with a lower petal spot RHS 43A.

*Color upper petals, lower surface.*—RHS N30A.

*Length of upper petals.*—3.1-3.3 cm.

*Width of upper petals.*—2.7 cm.

*Color lower petals, upper surface.*—RHS N30A.

*Color lower petals, lower surface.*—RHS N30A.

*Length of lower petals.*—2.9 cm.

*Width of lower petals.*—3.0 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 145A.

*Length of sepals.*—1.2 cm.

*Width of sepals.*—0.3-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.1 cm.

*Style color.*—RHS 53D.

*Style length.*—0.6-0.7 cm.

*Stigma color.*—RHS 53B.

*Ovary color.*—Between RHS 144A and RHS 144B.

*Ovary length.*—0.4-0.5 cm.

*Ovary diameter.*—0.2 cm.

Androecium:

*Number of stamens.*—6-8.

*Color of filaments.*—RHS N155B.

*Length filaments.*—0.7 cm.

*Anther color.*—RHS 45C.

*Length of anthers.*—0.2 cm.

*Color of pollen.*—RHS N30B.

*Pollen amount.*—Moderate.

*Fertility/seed set.*—Has not been determined to date.

*Disease/pest resistance.*—Has not been determined to date.

What is claimed is:

1. A new and distinct variety of *Pelargonium* plant named 'PEQZ0092' substantially as illustrated and described herein.

* * * * *